United States Patent [19]

Clemence et al.

[11] 4,100,291
[45] Jul. 11, 1978

[54] NOVEL 1,4-BENZODIOXANES

[75] Inventors: Francois Clemence, Paris; Daniel Humbert, Fontenay-sous-Bois, both of France

[73] Assignee: Roussel Uclaf, Paris, France

[21] Appl. No.: 791,927

[22] Filed: Apr. 28, 1977

[30] Foreign Application Priority Data

Apr. 30, 1976 [FR] France .................... 76 12941

[51] Int. Cl.² .............................. C07D 319/20
[52] U.S. Cl. .................. 424/267; 260/293.58; 260/296 B; 424/263
[58] Field of Search .......... 260/293.58, 296 B; 424/267, 263

[56] References Cited

U.S. PATENT DOCUMENTS

| | | | |
|---|---|---|---|
| 3,850,938 | 11/1974 | Derible et al. | 260/293.58 |
| 3,914,238 | 10/1975 | Soudijn et al. | 260/293.58 |
| 3,980,658 | 9/1976 | Possanza et al. | 260/296 B |
| 4,039,676 | 8/1977 | Huebner | 260/293.58 |

*Primary Examiner*—Norma S. Milestone

*Attorney, Agent, or Firm*—Hammond & Littell

[57] ABSTRACT

Novel 1,4-benzodioxanes of the formula

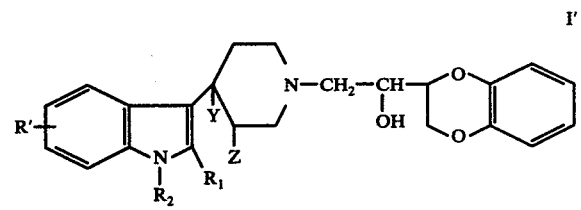

wherein R' is selected from the group consisting of hydrogen, alkoxy of 1 to 5 carbon atoms, chlorine, bromine and fluorine, $R_1$ and $R_2$ are individually selected from the group consisting of hydrogen and alkyl of 1 to 5 carbon atoms and Y and Z are hydrogen or together form a double bond in the form of their racemic mixtures or optically active isomers and their non-toxic, pharmaceutically acceptable acid addition salts having antihypertensive activity and a novel process and novel intermediates for their preparation.

19 Claims, No Drawings

NOVEL 1,4-BENZODIOXANES

STATE OF THE ART

Commonly assigned U.S. Pat. No. 3,850,938 and No. 3,947,578 describe piperidino-butyrophenones having central nervous system depressant activity. French Pat. No. 2,213,059 describes derivatives of 1,4-benzodioxanes as antihypertensive agents.

OBJECTS OF THE INVENTION

It is an object of the invention to provide the novel 1,4-benzodioxanes of formula I' and their non-toxic, pharmaceutically acceptable acid addition salts.

It is another object of the invention to provide a novel process for the preparation of the compounds of formula I' and to provide novel intermediates.

It is an additional object of the invention to provide novel antihypertensive compositions and to provide a novel method of reducing hypertension in warm-blooded animals.

These and other objects and advantages of the invention will become obvious from the following detailed description.

THE INVENTION

The novel products of the invention are selected from the group consisting of 1,4-benzodioxanes of the formula

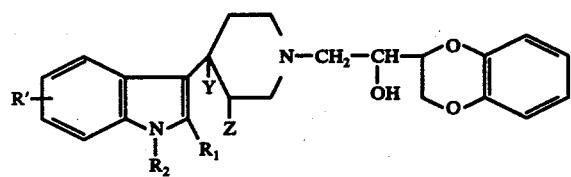

wherein R' is selected from the group consisting of hydrogen, alkoxy of 1 to 5 carbon atoms, chlorine, bromine and fluorine, $R_1$ and $R_2$ are individually selected from the group consisting of hydrogen and alkyl of 1 to 5 carbon atoms and Y and Z are hydrogen or together form a double bond in the form of their racemic mixtures or optically active isomers and their non-toxic, pharmaceutically acceptable acid addition salts.

Among the preferred compounds of the invention are compounds of the formula

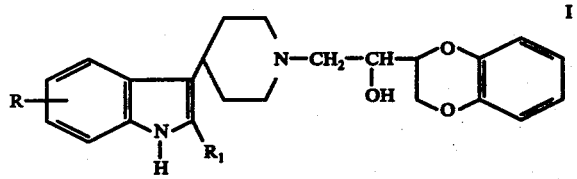

wherein R is selected from the group consisting of hydrogen and alkoxy of 1 to 5 carbon atoms and $R_1$ has the above definition and their non-toxic, pharmaceutically acceptable acid addition salts.

Examples of suitable alkoxy radicals are methoxy, ethoxy, propoxy, butoxy, sec.-butoxy or tert.-butoxy and suitable alkyls are methyl, ethyl, propyl, butyl, sec.-butyl, tert.-butyl and pentyl.

Examples of suitable acids for the formation of the acid addition salts are mineral acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartric acid, citric acid, oxalic acid, glyoxylic acid and aspartic acid, alkane monosulfonic acids and alkane disulfonic acids such as methanesulfonic acid, ethanesulfonic acid, propanesulfonic acid, methanedisulfonic acid and $\alpha,\beta$-ethanedisulfonic acid, and aryl monosulfonic acids and aryldisulfonic acids such as benzenesulfonic acid.

Among the preferred compounds of formula I' are those wherein R' is hydrogen, methoxy or chlorine, $R_1$ is hydrogen or methyl, $R_2$ is hydrogen or methyl, Y and Z are hydrogen or together form a double bond in the form of their racemic mixtures or optically active isomer and their non-toxic, pharmaceutically acceptable acid addition salts. Particularly preferred are the compounds of formula I wherein R is hydrogen or methoxy and $R_1$ is hydrogen or methyl and their acid addition salts.

The novel process of the invention for the preparation of the compounds of formula I' comprises reacting a compound of the formula

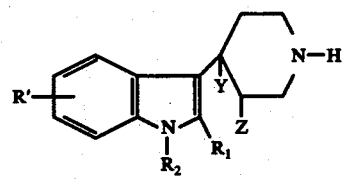

with a compound of the formula

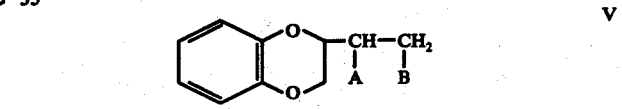

wherein A is OH and B is chlorine or bromine or A and B together form an epoxy oxygen to obtain the corresponding compound of formula I' which may be treated with an organic or inorganic acid to form the acid addition salt.

When the compound of formula V is a product in which A and B are an epoxy oxygen, the reaction of the compounds of formulae IV and V is preferably effected in an organic solvent such as aromatic hydrocarbons such as benzene, toluene or xylene, an alkanol such as methanol, ethanol or propanol, halogenated hydrocarbons such as methylene chloride or chloroform or mixtures of the solvents such as mixtures of a lower alkanol and an aromatic hydrocarbon.

Wherein A is OH and B is chlorine or bromine in the compound of formula V, the reaction is preferably effected in an organic solvent such as aromatic hydrocarbons like benzene, toluene or xylene; lower alkanols like ethanol, butanol or amyl alcohol; ketones such as acetone, methyl ethyl ketone or methyl isobutyl ketone; or ether such as dioxane or an amide such as dimethylformamide. Preferably the reaction is effected with an excess of the product of formula IV.

The said reaction is preferably effected in the presence of a basic agent such as an alkali metal carbonate or alkali metal bicarbonate and the reaction can be effected at a temperature ranging from room temperature to the reflux temperature of the mixture. The salification of the products of formula I' is preferably effected in a solvent or mixture of solvents such as water, acetone and ether.

The process for the preparation of compounds of formula I is preferably comprised of reacting a compound of the formula

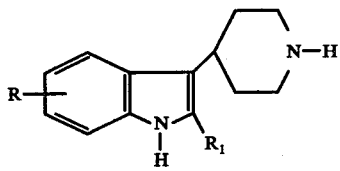

wherein R and $R_1$ have the above definition with a compound of the formula

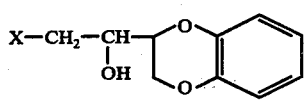

wherein X is chlorine or bromine to obtain the corresponding compound of formula I which may be salified, if desired, to form the corresponding acid addition salts.

The preferred conditions for the latter process comprises effecting the reaction in an organic solvent such as an aromatic hydrocarbon such as benzene, toluene or xylene; a lower alkanol such as ethanol, butanol or amyl alcohol; a ketone such as acetone, methyl ethyl ketone or methyl isobutyl ketone; an ether such as dioxane or an amide such as dimethylformamide. An excess of the compound of formula II is preferably used and the reaction is effected in the presence of a basic agent such as an alkali metal carbonate or bicarbonate. The reaction may be effected at a temperature ranging from room temperature to reflux of the reaction mixture. The salification of the compound of formula I with an acid may be effected in one or more solvents such as water, ether or acetone.

The products of formulae I' and I have 2 asymetrical carbon atoms and can exist in different forms of sterochemical optical isomers and the invention is intended to cover the different forms which can be separated by known means. The diastereoisomeric racemates are designated by the prefixes erythro and threo which can be separately obtained by known methods such as selective crystallization by chromatography in a column or by direct preparation of the product of formula I or I' starting with the desired form of the product of formula III or V respectively.

The erythro and threo racemates can be resolved into their optical enantiomeres by equally known methods such as formation of salts with optically active acids. The mixtures of the different isomers of the products of formulae I and I' and especially the mixtures of the diastereoisomeric racemates are within the scope of the invention.

The novel antihypertensive compositions of the invention are comprised of an antihypertensively effective amount of at least one compound of formula I' and an inert pharmaceutical carrier or excipient. The compositions may be in the form of tablets, dragees, gelules, granules, suppositories and injectable solutions or suspensions prepared in the usual manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, dispersants and emulsifiers.

The compositions due to their antihypertensive activity are useful in human theraphy for the treatment of arterial hypertensive of any form, permanent, slight, moderate or severe.

The novel method of the invention for relieving hypertension in warm-blooded animals, including humans, comprises administering to warm-blodded animals an antihypertensively effective amount of at least one compound of formula I' or its non-toxic, pharmaceutically acceptable acid addition salts. The compounds may be administered orally, rectally or parenterally and the usual daily dose is 1 to 50 mg/kg in humans by oral rout.

4-(2-methyl-3'-indolyl)-piperidine in the form of its optically active isomers or racemic form is a novel intermediate which may be prepared by reacting benzylpiperidone and 2-methyl-indole in acetic acid to obtain 4-(2-methyl -3-indolyl)-1-benzyl-1,2,3,6-tetrahydropyridine which is then reduced by gaseous hydrogen in the presence of a catalyst based on palladium.

Also novel intermediates are (dl) erythro 2,3-dihydro-2-oxyranyl-1,4-benzodioxine and (dl) threo 2,3-dihydro-2-oxyranyl-1,4-benzodioxane which two diastereo-isomeric racemates can be obtained separately by known methods such as chromatography of the mixture of racemates through a column.

The products of formula IV which are not known may be prepared by the process of French Pat. No. 2,193,584 or No. 2,227,873 or an analogous process or by the process of commonly assigned French application Ser. No. 76-25798. A product of the formula

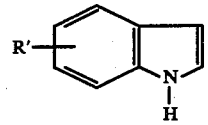

wherein R' is fluorine, chlorine or bromine is reacted with pyridine and acetyl chloride to obtain a compound of the formula

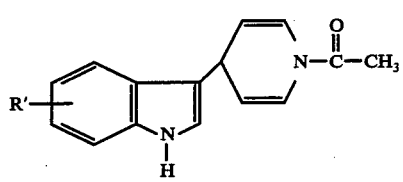

the latter is reduced to obtain a compound of the formula

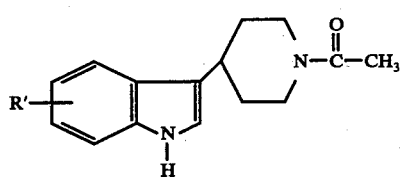

which is then hydrolyzed to obtain a compound of the formula

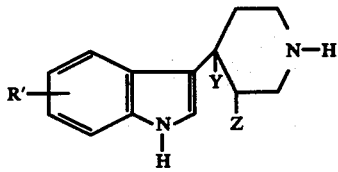

wherein Y and Z are hydrogen which may be isolated or reacted with an acid to form the corresponding salt.

Another method comprises reacting a compound of the formula

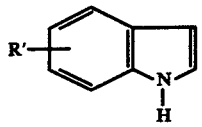   D wherein R' is hydrogen, alkoxy of 1 to 3 carbon atoms, fluorine, chlorine or bromine with 4-piperidone hydrochloride in acetic acid in the optional presence of a strong acid to obtain a salt of a compound of the formula

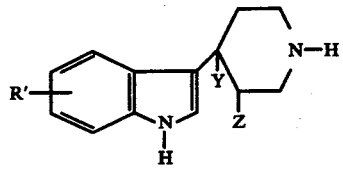

wherein Y and Z form a double bond which may be isolated in the form of a salt or the corresponding base which may be salified, if desired.

In the following examples there are described several preferred embodiments to illustrate the invention. However, it should be understood that the invention is not intended to be limited to the specific embodiments.

EXAMPLE 1

(d,l) erythro
α-(2,3-dihydro-1,4-benzodioxin-2-yl)-4-([1H]-indol-3-yl)-1-piperidine-ethanol hydrochloride A mixture of 8.5 g of α-(chloromethyl)-1,4-benzodioxin-2-methanol, 16 g of 4-([1H]-indol-3-yl)-piperidine and 150 ml of amyl alcohol was refluxed with stirring for 4 hours and the mixture was then allowed to return to room temperature. The mixture stood overnight and was then poured into a liter of ethyl ether. The mixture was filtered and the filtrate was concentrated to dryness. The residue was taken up in a N hydrochloric acid solution and the aqueous phase was removed by decanting. The oily phase was washed with ethyl ether and was then taken up in a mixture of methylene chloride - 2N sodium hydroxide. The mixture was stirred for 2 hours and was then decanted. The aqueous phase was extracted twice with methylene chloride and the combined methylene chloride phases were washed with water, dried and concentrated to dryness to obtain 9.5 g of row products. The raw product was treated with 200 ml of ethyl ether and the mixture was filtered. The filtrate was treated with 20 ml of a 5N hydrochloric acid solution and the mixture was vacuum filtered. The recovered precipitate was washed with ethyl ether to obtain 7 g of crystals and the latter was treated with activated carbon in methanol. The mixture was filtered and 250 ml of ethyl ether was added. The mixture was vacuum filtered to obtain 4.8 g of (d,l) erythro α-(2,3-dihydro-1,4-benzodioxin-2-yl)-4-([1H]-indol-3-yl)-piperidine-ethanol hydrochloride melting at 250° C.

| Analysis: | | | | | | | | | |
|---|---|---|---|---|---|---|---|---|---|
| Calculated: | %C | 66.57 | %H | 6.56 | %Cl | 8.55 | %N | 6.75 |
| Found: | | 66.4 | | 6.8 | | 8.4 | | 6.7 |

EXAMPLE 2

A and B isomers of (d,l)
α-2,3-dihydro-1,4-benzodioxin-2-yl)-4-(5-methoxy-[1H]-indol-3-yl)-1-piperidine-ethanol
and its hydrochloride

STEP A:

α-(2,3-dihydro-1,4-benzodioxin-2-yl)-4-(5-methoxy-([1H]-indol-3-yl)-1-piperidine-ethanol (mixture of 2 diastereoisomeric racemates A mixture of 4.6 g of 4-(5-methoxy-[1H]-indol-3-yl)-piperidine, 4.3 g of α-(chloromethyl)-1,4-benzodioxin-2-methanol, 4.4 g of sodium carbonate, 3.3 g of potassium iodide and 25 ml of dimethylformamide was heated with stirring at 100° C for 24 hours under a nitrogen atmosphere and then the mixture was cooled and filtered. The filter was washed with dimethylformamide and the filtrate was evaported under reduced pressure to dryness. The residue was taken up in a 1—1 mixture of water and methylene chloride and the organic phase was recovered by decantation, was washed, dried and evaporated to dryness under reduced pressure to obtain 9.1 g of α-(2,3-dihydro-1,4-benzodioxin-2-yl)-4-(5-methoxyl-[1H]-indol-3-yl)-1-piperidine-ethanol in the form of a mixture of 2 diastereoisomeric racemates in the form of a brown oil which was used as is for the next step.

STEP B: Separation of A and B isomers and formation of hydrochlorides

The oily residue of Step A was taken up in a 1—1 isopropyl ether-isopropanol mixture and crystallization was effected. The product was crystallized from acetonitrile to obtain 1.2 g of isomer A of (dl) α-(2,3-dihydro-1,4-benzodioxin-2-yl)-4-(5-methoxy-[1H]-indol-3-yl)-1-piperidine-ethanol in the form of a white solid melting at 214° C.

| Analysis: | | | | | | |
|---|---|---|---|---|---|---|
| Calculated: | %C | 70.56 | %H | 6.91 | %N | 6.86 |
| Found: | | 70.5 | | 6.7 | | 6.8 |

The said isomer A was dissolved in methanol and 1ml of 5N hydrochloric acid in ether was added which caused crystallization to occur. The mixture was vacuum filtered and the recovered product was washed successively with methanol and ether and dried under reduced pressure to obtain a 76% yield of the A isomer of (dl) α-(2,3-dihydro-1,4-benzodioxin-2-yl)-4-(5-methoxy-[1H]-indol-3-yl)-1-piperdine-ethanol hydrochloride in the form of a white solid melting at 250°–254° C.

| Analysis:     |    |       |    |      |    |      |    |      |
| ------------- | -- | ----- | -- | ---- | -- | ---- | -- | ---- |
| Calculated:   | %C | 64.78 | %H | 6.57 | %N | 6.30 | %Cl | 7.97 |
| Found:        |    | 64.9  |    | 6.7  |    | 6.3  |    | 8.1  |

The solvents used for the crystallizations of isomer A above were combined and concentrated to dryness. The residual oil was chromatographed over silica gel and was eluted with a 95-5 methylene chloride-methanol mixture. The first 15 fractions were concentrated and the resulting product was crystallized from acetonitrile to obtain 0.5 g of a product which was identified as isomer A above. The next 20 fractions were combined and evaporated to dryness. The crystalline residue was crystallized from isopropanol to obtain 1.2 g of isomer B of (dl) α-(2,3-dihydro-1,4-benzodioxin-2-yl)-4-(5-methoxy-[1H]-indol-3-yl)-1-piperidine-ethanol in the form of a white solid melting at 128°-130° C.

| Analysis:   |    |       |    |      |    |      |
| ----------- | -- | ----- | -- | ---- | -- | ---- |
| Calculated: | %C | 70.56 | %H | 6.91 | %N | 6.86 |
| Found:      |    | 70.3  |    | 6.8  |    | 6.9  |

The said isomer B was dissolved in methanol and a small quantity of 5N hydrochloric acid in ether was added thereto. The mixture was diluted with ether to effect crystallization. The product was crystallized from isopropanol for a 50% cyrstallization yield of the B isomer of (dl) α-(2,3-dihydro-1,4-benzodioxin-2-yl)-4-(5-methoxy-[1H]-indol-3-yl)-1-piperidine-ethanol hydrochloride in the form of a yellow white solid melting at 200°-202° C.

| Analysis:   |    |       |    |      |    |     |     |      |
| ----------- | -- | ----- | -- | ---- | -- | --- | --- | ---- |
| Calculated: | %C | 64.78 | %H | 6.97 | %N | 6.3 | %Cl | 7.97 |
| Found:      |    | 64.8  |    | 6.7  |    | 6.2 |     | 8.0  |

EXAMPLE 3

α-(2,3-dihydro-1,4-benzodioxin-2-yl)-4-(6-methoxy-2-methyl-[1H]-indol-3-yl)-1-piperidine-ethanol hydrochloride (mixture of 2 diastereoisomeric racemates)

3.6 g of 4-(6-methoxy-2-methyl-[1H]-indol-3-yl)-piperidine, 2.7 g of 2,3-dihydro-2-oxiranyl-1,4-benzodioxine and 0.1 g of hydroquione were added to 35 ml of benzene containing 1 ml of methanol and the mixture was refluxed under a nitrogen atmosphere for 2 hours and was then cooled. The mixture was poured into 3.5 ml of 5N hydrochloric acid in ether and the mixture was stirred at room temperature for 10 minutes to effect precipitation. The mixture was vacuum filtered and the recovered product was washed with benzene and then with ether to obtain 6.2 g of α-(2,3-dihydro-1,4-benzodioxin-2-yl)-4-(6-methoxy-2-methyl-[1H]-indol-3-yl)-piperidine-ethanol hydrochloride in the form of 2 diastereoisomeric racemate in the form of a white solid melting at 200°-203° C.

| Analysis:   |    |       |    |      |    |      |     |      |
| ----------- | -- | ----- | -- | ---- | -- | ---- | --- | ---- |
| Calculated: | %C | 65.42 | %H | 6.81 | %N | 6.10 | %Cl | 7.72 |
| Found:      |    | 65.4  |    | 6.9  |    | 6.3  |     | 8.0  |

EXAMPLE 4

α-(2,3-dihydro-1,4-benzodioxin-2-yl)-4-([1H]-indol-3-yl)-1,2,3,6-tetrahydro-1-pyridine-ethanol

STEP A:
4-([1H]-indol-3-yl)-1,2,3,6-tetrahydro-pyridine 50 ml of N aqueous phosphoric acid and 39.3 g of 4-piperidine-monohydrate hydrochloride were added with stirring under nitrogen to a solution of 10 g of indole in 200 ml of acetic acid heated at 95°-100° C and the mixture was heated for an hour at 100° C and then allowed to cool. The mixture was poured into 350 ml of concentrated ammonium hydroxide containing ice and the mixture was extracted with ethyl acetate. The organic extracts were washed with water and water containing sodium chloride, were dried over magnesium sulfate and evaporated to dryness to obtain 14.7 g of raw product. The latter was crystallized from 75 ml of methanol and the mixture was filtered under reduced pressure. The product was washed with methanol and ether to obtain 1.42 g of 4-([1H]-indol-3-yl)-1,2,3,6-tetrahydro-pyridine melting at 185°-186° C.

The mother liquors were evaporated to dryness and the residue was chromatographed over silica gel. Elution with a 6-3-1 chloroform-methanol-triethylamine mixture yielded 4.55 g of product with Rf = 0.15. The product was empasted with ether to obtain 4.295 g of the said pyridine for a total yield of 5.715 g. The product was purified from hot and cold isopropanol to obtain 3.56 g of 4-([1H]-indol-3-yl)-1,2,3,6-tetrahydropyridine melting at 190°-191° C.

STEP B:
α-(2,3-dihydro-1,4-benzodioxin-2-yl)-4-([1H]-indol-3-yl)-1,2,3,6-tetrahydro-pyridine-ethanol A mixture of 5 g of the product of Step A, 5.4 g of α-(chloromethyl)-1,4-benzodioxin-2-methanol, 5.5 g of sodium carbonate, 4.2 g of potassium iodide and 100 ml of dimethylformamide was heated at 100° C under nitrogen for 24 hours and was then cooled and filtered. The filtrate was poured into ice and the gum formed was extracted with methylene chloride. The organic phase was washed, dried over calcium chloride and evaporated to dryness. The brown oily residue was chromatographed over silica gel and was eluted with a 98-2 methylene chloride-methanol mixture. The combined eluates were evaporated to dryness and the residue was crystallized from isopropanol to obtain 2.5 g of α-(2,3-dihydro-1,4-benzodioxin-2-yl)-4-([1H]-indol-3-yl)-1,2,3,6-tetrahydro-1-pyridine-ethanol melting at 177° C.

| Analysis:   |    |       |    |      |    |      |
| ----------- | -- | ----- | -- | ---- | -- | ---- |
| Calculated: | %C | 73.38 | %H | 6.43 | %N | 7.44 |
| Found:      |    | 73.5  |    | 6.7  |    | 7.4  |

EXAMPLE 5

α-(2,3-dihydro-1,4-benzodioxin-2-yl)-4-(1-methyl-[1H]-indol-3-yl)-1-piperidine-ethanol A mixture of 12.5 g of 4-(1-methyl-[1H]-indol-3-yl)-piperidine hydrochloride, 10.7 g of 2,3-dihydro-2-oxiranyl-1,4-benzodioxin, 0.1 g of hydroquinone, 120 ml of benzene and 20 ml of methanol was refluxed with stirring under nitrogen for 2 hours and was then cooled and poured into 200 ml of ether to effect crystallization. The mixture was treated with 100 ml of aqueous 5% sodium bicarbonate solution and the organic phase was decanted. The aqueous phase was extracted with methylene chloride and the combined organic phases were washed with water until the wash water was neutral, dried, decolorized with activated carbon and evaporated to dryness. The 20 g of brown oil residue was chromatographed over silica gel and was eluted with a 95-5 methylene chloride-methanol mixture. Evaporation of the eluates was followed by crystallization of the residue from ethanol to obtain 8.6 g of α-(2,3-dihydro-1,4-benzodioxin-2-yl)-4-(1-methyl-[1H]-indol-3-yl)-1-piperidine-ethanol after a second crystallization from ethanol in the form of a white solid melting at 155° C.

Analysis:

| Calculated: | %C | 73.3 | %H | 7.19 | %N | 7.14 |
|---|---|---|---|---|---|---|
| Found: | | 73.7 | | 7.2 | | 7.1 |

EXAMPLE 6

α-(2,3-dihydro-1,4-benzodioxin-2-yl)-4-(5-chloro-[1H]-indol -3-yl)-1-piperidine-ethanol hydrochloride(mixture of 2 diastereoisomeric racemates)

STEP A:
1-acetyl-4-(5-chloro-[1H]-indol-3-yl)-1,4-dihydropyridine 27 ml of redistilled pyridine were added at an interior temperature of 8° to 15° C to 120 ml of dioxane and 11.2 ml of acetyl chloride cooled in an ice bath and then a mixture of 22 g of 5-chloro-1H-indole in 120 ml of dioxane was added thereto while keeping the temperature at 10° to 15° C. The mixture was then stirred for 7 hours at room temperature and protected from the light and the mixture was poured into 500 ml of water. The resulting mixture was stirred for 5 minutes and then another 500 ml of water were added thereto. The mixture was filtered and the product was empasted with 40 ml of acetonitrile and then was filtered. The product was rinsed with acetonitrile and once with ether to obtain 13.5 g of 1-acetyl-4-(5-chloro-[1H]-indol-3-yl)-1,4-dihydro-pyridine in the form of a pale yellow solid melting at 202° C.

Analysis:

| Calculated: | %C | 66.06 | %H | 4.80 | %Cl | 13.0 | %N | 10.27 |
|---|---|---|---|---|---|---|---|---|
| Found: | | 66.0 | | 4.9 | | 13.1 | | 10.4 |

STEP B:
1-acetyl-4-(5-chloro-[1H]-indol-3-yl)-piperidine

Hydrogen was absorbed into a mixture of 8.49 g of the product of Step A, 850 mg of platinum oxide and 420 ml of ethanol until saturated and the mixture was filtered. The filter was rinsed with ethanol and the filtrate was evaporated to dryness to obtain 9 g of raw product. The latter was taken up in 10 ml of acetonitrile and the mixture was stirred at room temperature for 20 minutes and was then filtered. The product was rinsed with acetonitrile to obtain 6.99 g of 1-acetyl-4-(5-chloro-[1H]-indol-3-yl)-piperidine which was purified from hot and cold ethanol. After drying, there were obtained 4.78 g of the said product in the form of a colorless solid melting at 201° C.

Analysis:

| Calculated: | %C | 65.1 | %H | 6.19 | %Cl | 12.81 | %N | 10.12 |
|---|---|---|---|---|---|---|---|---|
| Found: | | 65.2 | | 6.3 | | 12.6 | | 10.1 |

STEP C: 4-(5-chloro-[1H]-indol-3-yl)-piperidine

A mixture of 6.02 g of the product of Step B, 6 g of potassium hydroxide and 50 ml of propanol was refluxed for 4 hours and was then cooled and poured into 500 ml of ice water. The mixture was stirred for 45 minutes at room temperature and was filtered. The recovered product was rinsed with water and dried under reduced pressure at 50° C to obtain 5.02 g of 4-(5-chloro-[1H]-indol-3-yl)-piperidine melting at 208° C.

STEP D:
α-(2,3-dihydro-1,4-benzodioxin-2-yl)-4-(5-chloro-[1H]-indol-3-yl)-1-piperidine-ethanol hydrochloride (mixture of 2 diastereoisomeric racemates A mixture of 7 g of the product of Step C, 8.43 g of 2,3-dihydro-2-oxiranyl-1,4-benzodioxine, 50 ml of benzene and 2 ml of methanol was refluxed under nitrogen for 4 hours and after cooling, 6.5 ml of 5N hydrochloric acid in ether were added thereto dropwise. The mixture was vacuum filtered and the product was washed successively with bezene and ether and dried. The product was crystallized from methanol and and was decolorized with activated carbon to obtain 10.1 g of α-(2,3-dihydro-1,4-benzodioxin-2-yl)-4-(5-chloro-[1H]-indol-3-yl)-piperidine hydrochloride in a mixture of 2 diastereoisomeric racemates as a white solid melting at 210° C Analysis:

| Calculated: | %C | 61.47 | %H | 5.83 | %Cl | 15.78 | %N | 6.23 |
|---|---|---|---|---|---|---|---|---|
| Found: | | 61.2 | | 5.9 | | 15.7 | | 6.4 |

EXAMPLE 7 erythro α-(2,3-dihydro-1,4-benzodioxin-2-yl)-4-(2-methyl-[1H]-indol-3-yl)-1-piperidine-ethanol hydrochloride

STEP A:
1-benzyl-4-(2-methyl-[1H]-indol-3-yl)-1,2,3,6-tetrahydro-pyridine hydrochloride 37.8 g of benzyl piperidone were added with stirring at room temperature over 10 minutes to a solution of 13.1 g of 2-methyl-1H-indole in 160 ml of acetic acid and the mixture was stirred for 24 hours and then was poured into a mixture of ice and concentrated ammonium hydroxide. The gum formed was taken up in methylene chloride and the organic phase was washed, dried and evaporated to dryness to obtain 45.6 g of an oily product. The latter was taken up in 200 ml of methylene chloride and the organic phase was decanted. An equal quantity of a concentrated solution of sodium bisulfite and 800 ml of water was added and the mixture was stirred for 2 hours. The mixture was decanted again and the aqueous phase was extracted with methylene chloride. The combined organic phase were washed, dried and evaporated to dryness and the residue was dissolved in 100 ml of isopropanol. 20 ml of 5N hydrochloric acid in ethanol was added to the solution and the mixture was iced for 2 hours. The precipitate formed was recovered by vacuum filtration, was washed with isopropanol and dried under reduced pressure at 60° C to obtain 27.7 g 1-benzyl-4-(2-methyl-[1H]-indol -3-yl)-1,2,3,6-tetrahyro-pyridine hydrochloride with the form of a yellow solid melting at ≈210° C with decomposition.

| Analysis: | | | | | | | | | |
|---|---|---|---|---|---|---|---|---|---|
| Calculated: | %C | 74.43 | %H | 6.84 | %N | 8.27 | %Cl | 10.46 |
| Found: | | 74.6 | | 6.8 | | 8.2 | | 10.6 |

STEP B: 4-(2-methyl-[1H]-indol-3-yl)-piperidine

A mixture of 470 ml of ethanol, 23.7 g of the product of Step A and 4.7 g of 10% palladized carbon was placed in a hydrogenation vessel and hydrogen was introduced until 2910 ml of hydrogen were absorbed (theoretical - 3 liters). The catalyst was filtered off and the filtrate was evaporated to dryness under reduced pressure. The residue was crystallized from isopropanol to obtain 11.7 g of a hydrochloride salt. 5.5 g of the said salt were dissolved in 100 ml of water and then 100 ml of methylene chloride and 10 g of potassium carbonate were added in small fractions. The mixture was stirred vigorously for one hour and the organic phase was decanted. The aqueous phase was extracted with methylene chloride and the combined organic phases were washed, dried and evaporated to dryness. The residue was crystallized from isopropanol to obtain 3.4 g of 4-(2-methyl[1H]-indol-3-yl)-piperidine in the form of a cream white solid melting at 210° C.

| Analysis: | | | | | | | |
|---|---|---|---|---|---|---|---|
| Calculated: | %C | 78.46 | %H | 8.47 | %N | 13.07 |
| Found: | | 78.6 | | 8.5 | | 12.6 |

STEP C: (dl) erythro 2,3-dihydro-2-oxiranyl-1,4-benzodioxine

Using the procedure of Rosnati et al [Tetrahedron, Vol. 18 (1962), p. 289–98], a diastereoisomeric racemate mixture of 2,3-dihydro-2-oxiranyl-1,4-benzodioxine was prepared. 4.5 g of the said mixture was chromatographed with 210 g of silica H and elution with a 90-10 cyclohexane-ethyl acetate mixture yielded two principal fractions which were evaporated to dryness. One fraction resulted in 2.1 g of (dl) 2,3-dihydro-2-oxiranyl-1,4-benzodioxine with a melting point of 51°–52° C and an RMN spectrum (Deuterochloroform - 60Hz): hydrogen stituated in carbon in the 1-position of a 2-oxiranyl ring and a multiplet at 162 to 180 Hz. The second fraction resulted in 1.6 g of (dl) 2,3-dihydro-2-oxiranyl-1,4-benzodioxine with a melting point of 30° C and an RMN spectrum (Deuterochloroform-60Hz): hydrogen's on the carbon in the 1-position of 2-oxiranyl ring - doublet at 172–175 Hz.

14 g of the said product melting at 51 to 52° C were added at less than 30° C with stirring to 280 ml of methanol saturated with ammonia and the mixture was stirred for 6 hours which bubbling ammonia therethrough. The methanol was evaporated to obtain 15.8 g of raw product which was dissolved in 20 ml of refluxing methanol. The solution was concentrated in half and 60 ml of isopropyl ether were added thereto. The mixture stood and was then filtered. The recovered prouct was rinsed twice with isopropyl ether to obtain 11.3 g of (dl) α-aminomethyl-2,3-dihydro-1,4-benzodioxin-2-methanol with a melting point of 98°–100° C. The purified product melted at 103°–104° C. The RMN spectrum: constant of a mixture in which the 2 hydrogens situated on the carbon in the 2-position of the benzodioxine ring and the carbon of methanol J ≃ 7 Hz which is the constant of the erythro isomer.

Using the same procedure, 14.5 g of the product melting at 30° C were reacted to obtain 12 g of (dl) α-aminomethyl-2,3-dihydro-1,4-benzodioxin-2-methanol melting at 86° to 88° C. After crystallization from isopropyl ether, the product melted at 90°–91° C. The RMN spectrum showed a constant of a mixture in which the 2 hydrogens situated on the carbon at the 2-position of the benzodioxine ring and the carbon of methanol - J = 3 Hz which is the threo isomer.

STEP D: (dl) erythro α-(2,3-dihydro-1,4-benzodioxin-2-yl)-4-(2-methyl-[1H]-indol-3-yl)-1-piperidine-ethanol hydrochloride A mixture of 3.4 g of 4-(2-methyl-[1H]-indol-3-yl)-piperidine, 3.56 g of erythro 2,3-dihydro-2-oxiranyl-1,4benzodioxine, 0.1 g of hydroquinone, 5 ml of methanol and 50 ml of benzene was refluxed for 2 hours under a nitrogen atmosphere and the mixture was cooled and decolorized with activated carbon. 3.5 ml of 5N hydrochloric acid in ether were added to the mixture which was then vacuum filtered. The recovered product was washed with benzene, dried under reduced pressure at 50° C and crystallized from isorpropanol to obtain 3.5 g of (dl) erythro α-(2,3-dihydro-1,4-benzodioxin-2-yl)-4-(2-methyl-[1H]-indol-3-yl)-1-piperidine-ethanol hydrochloride in the form of a white solid melting at 140° C with decomposition.

| Analysis: | | | | | | | | | |
|---|---|---|---|---|---|---|---|---|---|
| Calculated: | %C | 67.2 | %H | 6.81 | % N | 6.53 | %Cl | 8.27 |
| Found: | | 67.3 | | 7.0 | | 6.3 | | 8.3 |

EXAMPLE 8

(dl) erythro α-(2,3-dihydro-1,4-benzodioxin-2-yl)-4-([1H]-indol-3-yl)-1-piperidine-ethanol and its hydrochloride A mixture of 5 g of 4-([1H]-indol-3-yl)-piperidine, 4.9 g of (dl) erythro 2,3-dihydro-2-oxiranyl-1,4-benzodioxine, 20 ml of methanol and 100 ml of anhydrous benzene was refluxed for 3 hours under nitrogen and the mixture was then evaporated to dryness. The gummy residue was taken up in 50 ml of ethyl acetate which was then evaporated to dryness under reduced pressure. The residue was taken up in isopropyl ether and the mixture was filtered. The filtrate was evaporated to dryness under reduced pressure and the residue crystallized upon cooling. The product was crystallized from isopropanol to obtain 8 g of (dl) erythro α-(2,3-dihydro-1,4-benzodioxin-2yl)-4-([1H]-indol-3-yl)-1-piperidine-ethanol melting at 145° C. The RMN spectrum showed a constant of a mixture in which the proton in the 2-position of the benzodioxine ring and the proton situated on the carbon atom carrying the OH group: J ≃ 7 Hz which is the erythro isomer.

6 ml of 5N hydrochloric acid in ether were added at 25° C to a solution of 7.8 g of the above product in 100 ml of isopropanol and crystallization occurred upon cooling. The mixture was vacuum filtered and the recovered product was dried and crystallized from isopropanol and then methanol to obtain 5.5 g of (dl) erythro α-(2,3-dihydro-1,4-benzodioxin-2-yl)-4-([1H]-indol-3-yl)-1-piperidine-ethanol hydrochloride in the form of a whilte solid melting at ≃ 250° C with decomposition which was identical to the product of Example 1.

| Analysis: | | | | | | | | |
|---|---|---|---|---|---|---|---|---|
| Calculated: | %C | 66.57 | %H | 6.56 | %N | 6.75 | %Cl | 8.55 |
| Found: | | 66.4 | | 6.8 | | 6.6 | | 8.4 |

EXAMPLE 9

(dl) threo α-(2,3-dihydro-1,4-benzodioxin-2-yl)-4-([1H]-indol-3-yl)-1-piperidine-ethanol and its hydrochloride A mixture of 2.5 g of 4-([1H]-indol-3-yl)-piperidine, 2.5 g of (dl) threo 2,3-dihydro-2-oxiranyl-1,4-benzodioxin, 3 ml of methanol and 50 ml of benzene was refluxed for 6 hours under nitrogen and the mixture was cooled. The solvents were evaporated and the residue was crystallized from isopropanol to obtain 3.4 g of (dl) threo α-(2,3-dihydro-1,4-benzodioxin-2-yl)-4-([1H]-indol-3-yl)-1-piperidine-ethanol in the form of a white solid melting at 138°–139° C.

| Analysis: | | | | | | |
|---|---|---|---|---|---|---|
| Calculated: | %C | 72.99 | %H | 6.92 | %N | 7.4 |
| Found: | | 73.1 | | 7.1 | | 7.4 |

RMN spectrum: shows a mixture with a proton in the 2-position of the benzodioxine ring and proton situated on the carbon carrying the OH group: J ≃ 3 Hz which is the threo isomer.

2.2 ml of 5N hydrochloric acid in ether were added to a solution of 3.2 g of the above base in 50 ml of methanol and after crystallization, the mixture was vacuum filtered. The recovered product was washed with ether and dried to obtain 2.9 of (dl) threo α-(2,3-dihydro-1,4-benzodioxin-2-yl)-4-([1H]-indol-3-yl)-1-piperidine-ethanol hydrochloride in the form of a cream white solid melting at ≃ 260° C with decomposition.

| Analysis: | | | | |
|---|---|---|---|---|
| Calculated: | %C | 66.57 | %H | 6.56 |
| Found: | | 66.8 | | 6.6 |

EXAMPLE 10

(dl) erythro α-(2,3-dihydro-1,4-benzodioxin-2-yl)-4-([1H]-indol-3-yl)-1,2,3,6-tetrahydro-1-pyridine and its hydrochloride A mixture of 4 g of (dl) erythro 2,3-dihydro-2-oxiranyl-1,4-benzodioxine, 4 g of 1,2,3,6-tetrahydro-4-([1H]-indo-3-yl)-pyridine, 5 ml of methanol and 50 ml of benzene was refluxed with stirring for 2 hours and after cooling to room temperature, the mixture was vacuum filtered. The recovered precipitate was washed with benzene and dried to obtain 7.1 g of (dl) erythro α-(2,3-dihydro-1,4-benzodioxin -2-yl)-4-([1H]-indol-3-yl)-1,2,3,6-tetrahydro-1-pyridine-ethanol melting at 190° C.

| Analysis: | | | | | | |
|---|---|---|---|---|---|---|
| Calculated: | %C | 73.38 | %H | 6.43 | %N | 7.44 |
| Found: | | 73.1 | | 6.4 | | 7.3 |

5 ml of 5N hydrochloric acid in ether were added to a solution of 6.6 g of the above base in 50 ml of dimethylformamide and 250 ml of ether were added thereto. The mixture was evaporated to dryness and the residue was crystallized from 50 ml of isopropyl alcohol. The product was vacuum filtered to obtain 7.5 g of raw product which was dried and crystallized from 100 ml of methanol to obtain 7 g of (dl) erythro α-(2,3-dihydro-1,4-benzodioxin-2-yl)-4-([1H]-indol-3-yl)-1,2,3,6-tetrahydro-1-pyridine-ethanol melting at 260° C.

| Analysis: | | | | | | | | |
|---|---|---|---|---|---|---|---|---|
| Calculated: | %C | 66.90 | %H | 6.10 | %N | 6.78 | %Cl | 8.59 |
| Found: | | 67.2 | | 6.0 | | 6.8 | | 8.4 |

EXAMPLE 11

(dl) erythro α-(2,3-dihydro-1,4-benzodioxin-2-yl)-4-(6-methoxy-2-methyl-[1H]-indol-3-yl)-1-piperidine-ethanol hydrochloride A mixture of 7.13 g of (dl) erythro 2,3-dihydro-2-oxiranyl-1,4-benzodioxine, 7.33 g of 4-(2-methyl-6-methoxy-indol-3-yl)-piperidine, 5 ml of methanol and 50 ml of anhydrous benzene was refluxed with stirring under nitrogen for 3 hours and after cooling to 15° C, 7 ml of 5N hydrochloric acid in ether were added thereto. The mixture was vacuum filtered and the recovered product was washed 3 times with 50 ml of benzene and dried under reduced pressure at 80° C to obtain 13.4 g of (dl) erythro α-(2,3-dihydro-1,4-benzodioxin-2-yl)-4-(6-methoxy-2-methyl-[1H]-indol-3-yl)-1-piperidine-ethanol hydrochloride melting at ≃ 140° C.

| Analysis: | | | | | | | | |
|---|---|---|---|---|---|---|---|---|
| Calculated: | %C | 65.42 | %H | 6.81 | %N | 6.10 | %Cl | 7.72 |
| Found: | | 65.3 | | 6.8 | | 5.9 | | 7.9 |

EXAMPLE 12

Tablets were prepared from 300 mg of (dl) erythro α-(2,3-dihydro-1,4-benzodioxin-2-yl)-4-([1H]-indol-3-yl)-1-piperidine-ethanol hydrochloride and sufficient excipient of talc, aerosil and magnesium stearate to obtain a final tablet of 350 mg.

Gelules were prepared from 300 mg of the same product and sufficient excipient of talc, aerosil and magnesium stearate to obtain a final gelule of 350 mg.

PHARMACOLOGICAL DATA

A. Acute toxicity

The acute toxicity was determined on groups of 10 mice weighing 18 to 22 g and the products were administered intraperitoneally in suspension in carboxymethylcellulose and the animals were observed for one week and the $LD_{50}$ was determined. The results are in Table I.

TABLE I

| Product of Example | LD$_{50}$ in mg/kg |
|---|---|
| 1 | ≃ 100 |
| 2 - isomer A | ≃ 500 |
| 5 | ≃ 250 |

B. Hypotensive Activity

The hypotensive activity was determined on male rats of the Sprague-Dawley SPF strain weighing about 300 g which had been anestesized with nembutal (50 mg/kg intraveinously). The product was administered intraveinously by the jugular vein and the carotidine arterial pressure was measured before and after the administration of the test product. Table II reports the variations expressed in percent of arterial pressure after administration of the test product as compared to the initial arterial pressure as well as the time necessary for the pressure to return to the initial value.

TABLE II

| Product of Example | Dose in mg/kg | % Variation in pressure | Duration of Activity - min. |
|---|---|---|---|
| 1 | 1 | −25 | 45 |
| 1 | 0.1 | −10 | 30 |
| 2 isomer A | 1 | −14 | 60 |
| 2 isomer B | 1 | −20 | 60 |
| 3 | 1 | − 8 | 60 |
| 3 | 10 | −25 | 60 |
| 5 | 1 | −10 | 30 |

C. Antihypertensive Activity

The antihypertensive activity was determined on spontaneous hypertendus male rats of the Okamoto strain 8 weeks old and the test products were orally administered daily for 9 days. The arterial pressure was measured at the rat's tail by means of a pneumatic collar connected to an electronic transducer of pressure. The pressure was measured before and after the administration of the test product and Table III reports the variations expressed in percentage of arterial pressure after administration as compares to the initial pressure.

TABLE III

| Product of Example | Daily dose in mg/kg | % Pressure variation 1st Day 1 hr after 1st ad. | % Pressure variation 1st Day 4 hr. after | % Pressure variation 10th Day 24 hr. after 1st ad. |
|---|---|---|---|---|
| 1 | 50 | −11 | −12 | −15 |
| 3 | 50 | −26 | −27 | − 9 |
| 4 | 50 | −10 | −18 | − 3 |

Various modifications of the product or processes of the invention may be made without departing from the spirit or scope thereof and it is to be understood that the invention is to be limited only as defined in the appended claims.

We claim:

1. A compound selected from the group consisting of 1,4-benzodioxanes of the formula

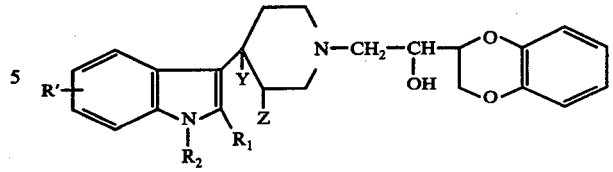

wherein R' is selected from the group consisting of hydrogen, alkoxy of 1 to 5 carbon atoms, chlorine, bromine and fluorine, R$_1$ and R$_2$ are individually selected from the group consisting of hydrogen and alkyl of 1 to 5 carbon atoms and Y and Z are hydrogen or together form a double bond in the form of their racemic mixtures or optically active isomers and their non-toxic, pharmaceutically acceptable acid addition salts.

2. A compound of claim 1 wherein R' is selected from the group consisting of hydrogen and alkoxy of 1 to 5 carbon atoms, Y and Z are hydrogen and R$_2$ is hydrogen.

3. A compound of claim 1 wherein R' is selected from the group consisting of hydrogen, CH$_3$O— and chlorine, R$_1$ and R$_2$ are individually selected from the group consisting of hydrogen and CH$_3$—.

4. A compound of claim 2 wherein R' is selected from the group consisting of hydrogen and methoxy and R$_1$ is selected from the group consisting of hydrogen and methyl.

5. A compound of claim 1 selected from the group consisting of racemic mixtures and optically active isomers of α-(2,3-dihydro-1,4-benzodioxin-2-yl)-4-([1H]-indol-3-yl)-1-piperidine-ethanol and its hydrochloride.

6. A compound of claim 1 selected from the group consisting of racemic mixtures and optically active isomers of α-(2,3-dihydro-1,4-benzodioxin-2-yl)-4-(6-methoxy-2-methyl[1H]-indol-3-yl)-1-piperidine-ethanol and its hydrochloride.

7. An antihypertensive composition comprising an antihypertensively effective amount of at least one compound of claim 1 and an inert pharmaceutical carrier.

8. A composition of claim 7 wherein R' is selected from the group consisting of hydrogen and alkoxy of 1 to 5 carbon atoms, Y and Z are hydrogen and R$_2$ is hydrogen.

9. A composition of claim 7 wherein R' is selected from the group consisting of hydrogen, CH$_3$O— and chlorine, R$_1$ and R$_2$ are individually selected from the group consisting of hydrogen and CH$_3$—.

10. A composition of claim 7 wherein R' is selected from the group consisting of hydrogen and methoxy and R$_1$ is selected from the group consisting of hydrogen and methyl.

11. A composition of claim 7 wherein the compound is selected from the group consisting of racemic mixtures and optically active isomers of α-(2,3-dihydro-1,4-benzodioxin-2-yl)-4-([1H]-indol-3-yl)-1-piperidine-ethanol and its hydrochloride.

12. A composition of claim 7 wherein the compound is selected from the group consisting of racemic mixtures and optically active isomers of α-(2,3-dihydro-1,4-benzodioxin-2-yl)-4-(6-methoxy-2-methyl-[1H]-indol-3-yl)-piperidine-ethanol and its hydrochloride.

13. A method of relieving hypertension in warm-blooded animals comprising administering to warm-blooded animals an antihypertensively effective amount of at least one compound of claim 1.

14. A method of claim 13 wherein R' is selected from the group consisting of hydrogen and alkoxy of 1 to 5 carbon atoms, Y and Z are hydrogen and $R_2$ is hydrogen.

15. A method of claim 13 wherein R' is selected from the group consisting of hydrogen, $CH_3O-$ and chlorine, $R_1$ and $R_2$ are individually selected from the group consisting of hydrogen and $CH_3-$.

16. A method of claim 13 wherein R' is selected from the group consisting of hydrogen and methoxy and $R_1$ is selected from the group consisting of hydrogen and methyl.

17. A method of claim 13 wherein the compound is selected from the group consisting of racemic mixtures and optically active isomers of α-(2,3-dihydro-1,4-benzodioxin -2-yl)-4-([1H]-indol-3-yl)-1-piperidine-ethanol and its hydrochloride.

18. A method of claim 13 wherein the compound is selected from the group consisting of racemic mixtures and optically active isomers of α-(2,3-dihydro-1,4-benzodioxin -2-yl)-4-(6-methoxy-2-methyl-[1H]-indol-3-yl)-1-piperidine-ethanol and its hydrochloride.

19. A compound selected from the group consisting of racemates and optically active isomers of 4-(2-methyl-3-indolyl)-piperidine, (dl) erythro 2,3-dihydro-2-oxiranyl-1,4-benzodioxine and (dl) threo 2,3-dihydro-2-oxiranyl-1,4-benzodioxine.

* * * * *